US00PP08540P

United States Patent [19]

Rotolante

[11] Patent Number: Plant 8,540

[45] Date of Patent: Jan. 11, 1994

[54] ANTHURIUM 'RUTH MORAT'

[75] Inventor: Denis W. Rotolante, Homestead, Fla.

[73] Assignee: Oglesby Plant Laboratories, Inc., Altha, Fla.

[21] Appl. No.: 21,142

[22] Filed: Feb. 23, 1993

[51] Int. Cl.[5] ..... A01H 5/00

[52] U.S. Cl. ..... Plt./88.1

[58] Field of Search ..... Plt. 88.1

*Primary Examiner*—James R. Feyrer

*Attorney, Agent, or Firm*—Frank B. Robb

[57] ABSTRACT

A hybrid Anthurium plant which is fast growing and freely branching, with very abundant year around flowering, with a mature plant having six to ten, dark red flowers, held consistently above the foliage.

1 Drawing Sheet

GENERAL DESCRIPTION OF THE INVENTION

There is disclosed a hybrid Anthurium plant whose seed parent is Anthurium antioquiense and the pollen parent a plant discovered by me and the subject of U.S. Plant Pat. No. 7,760, further being designated in my records as Anthurium Rotolante #1.

The plant hereof which I have chosen to designate as Anthurium 'Ruth Morat', is one of the products of a breeding program which I have carried on for some time both at my greenhouse in Homestead, Fla. and at Altha, Fla., and in this instance my new plant was the result of using the seed parent, with the pollen parent, a cultivar previously mentioned as being Rotolante #1 Anthurium.

I have caused the new plant to be asexually reproduced by tissue culture in Altha, Fla., and continuing to the present time, establishing that the plants come true in successive generations.

My new plant may generally be described as fast growing, compact, and freely branching, flowering early, and year around in exceptionally abundant form.

A mature plant often has 6–10 dark red flowers, dark leaves, the flowers being held above the foliage so as to provide an attractive pot plant, which is the kind of result I was hoping to obtain from the outset of my program.

In the following detailed description it will be noted that I have elaborated on the characteristics in many instances in an effort to provide a complete, thorough description, which is related to the drawing wherein.

Figure 1:
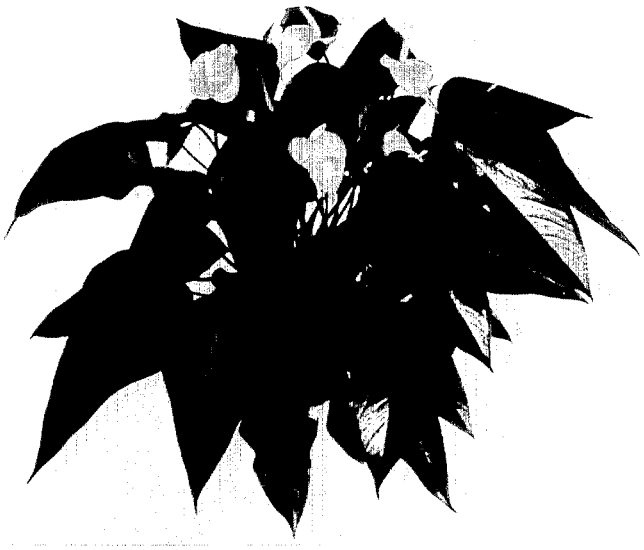
FIG. 1 is a view of the plant in typical flowering form.
Figure 2:
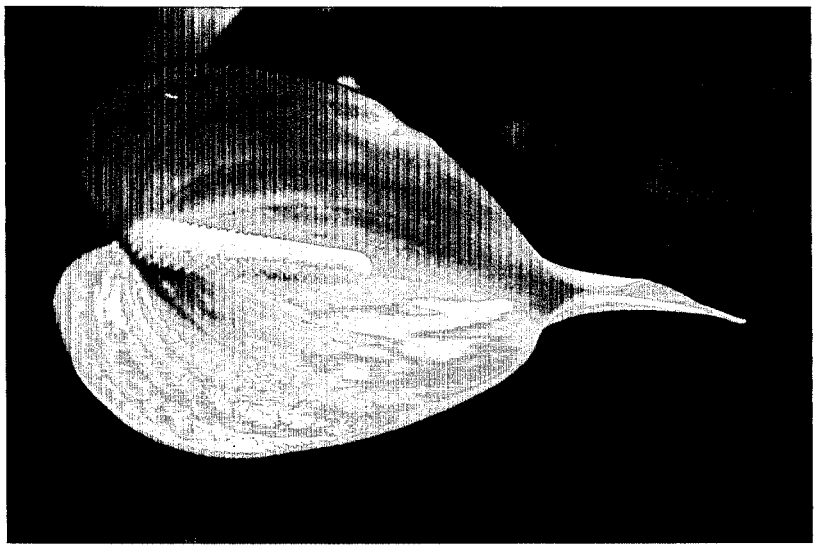
FIG. 2 is a full size flower head, both figures being photographic reproductions in as nearly true colors as possible to provide, with color designations related to The Royal Horticultural Society Colour Chart.

Parentage:

*Seed parent.*—Anthurium antioquiense.

*Pollen parent.*—Anthurium (Rotolante #1), U.S. Plant Pat. No. 7,760.

Classification: Anthurium hybrid.

Plant descriptions: Measurements and colors were taken from mature plants grown in 8-inch diameter pots in Altha, Fla. The five newest, fully developed units of each organ type were measured from each plant.

Stem: Smooth, yellow-green (144 D).

Lenticels: Not obvious.

Petioles: 28–39 cm. Smooth. Young petioles, yellow-green (144 A-B) on entire abaxial side and lower half of adaxial side. Upper half of adaxial side has variable amounts of grayed-red coloration (178 A-B) with visible green lenticels. Mature petioles, yellow-green (144 A) on all sides with uppermost 2.5–3.0 cm adjacent to the leaf blade swollen and often preserving grayed-red color (178 B) on the adaxial side.

Leaves: Ovate, acuminate tip. The leaf base shape depends on the stage of overall plant maturity when the leaf is formed. Leaves of young plants have obtuse leaf bases. Leaves of mature plants have leaf bases that are more truncate. Most leaves are slightly asymmetric. At maturity, leaves range from 26–33 cm long by 15–20 cm wide. Mature leaf blades are almost horizontal, forming an angle of approximately 90 degrees or more with the petioles. Margins entire.

*Color.*—Young expanding leaf yellow-green (initially between 146 A and 147 A, later closer to 147 A) adaxial, and yellow-green (146 A-B, 147 B) abaxial. Polished. Mature leaf yellow-green (darker than 147 A) adaxial, yellow-green (146 A-B) abaxial. Dull.

*Veins.*—Midrib and lateral veins prominent near base of the leaf blade. In this area, midrib and usually inner lateral veins protrude from leaf surface. In remainder of leaf blade they are even to somewhat sunken in the leaf surface. The outermost lateral veins are sunken. On the mature leaf, color of the veins from the base of leaf blade to the midsection (for midrib to approx. ⅔ of its length) yellow-green (146 A-B), lighter than that of the blade. In the case of young leaves (nearly fully expanded to fully expanded) it is usually grayed-red (178 A-D) similar to that of the upper part of the petiole. Color of the remaining part of the veins approximate the leaf surface color for young and mature leaves.

Leaf sheath: 10–18 cm long. Surrounds young leaf during early developmental stages and is directly attached to the stem below the leaf attachment. The leaf sheath surrounding the youngest leaf is yellow-green (144 B-C). With age it becomes slightly darker (144 A).

Flower:

*Type.*—Spathe and spadix. Spathe tightly rolled around spadix during development. The spathe is polished, smooth, ovate, cordate base, acuminate tip, 5.5–7.5 cm wide by 8.5–11.5 cm long; with a width to length ratio of 0.6:1 to 0.7:1. Newly opened flowers have a slight fragrance.

*Spathe.*—Color — Newly opened flower red (similar to 53 B) adaxial and red (51 A-B) abaxial. Mature flowers are red (similar to 53 C adaxial and 51 B abaxial). Aging flowers slowly fade. Veins — Inconspicuous. Midrib sunken in the spathe surface. Other veins in basal ⅓ of spathe sunken in slightly elevated ridges. Peduncle — 35–52 cm long. Lower half, yellow-green (144 A). Color of the upper part changes with flower development. Before spathe opens it is yellow-green (144 A-B) with a variable amount of red (46 B) mainly on the abaxial side immediately next to spathe. After opening of spathe, the adjacent zone is grayed-red (178 A-D depending on age and distance from spathe) adaxial and red (46 A-B) abaxial. The colors slightly fade with age but are visible even on aging peduncles, especially on abaxial side (178 B).

Reproductive organs:

*Spadix.*—5–7 cm long, 7–9 mm wide at base. When young, spadix color is red (56 D) at the base merging with gradations of red (56 C, 56 B, 56 A) of the middle zone which then merges with a different red (54 B) at the tip. With maturity the lower ½ to ⅔ of spadix becomes much darker red (54 A-B); while the zone near the tip becomes lighter (54 C-D). The tip remains darker (54 A-C).

Stamens: Anthers and filaments not clearly visible.

Flowering:

*Time.*—After approximately 6 months in a 5- to 6-inch diameter pot, 3–5 open blossoms will be present depending on season.

*Roots.*—Roots developed above soil line are fleshy and non-branching. Roots developed below the soil line are fleshy and well branched with fine lateral roots.

*Diseases.*—No unusual susceptibility to diseases noted to date.

*Insects.*—No unusual susceptibility to insects noted to date.

General observations: Anthurium 'Ruth Morat' is fast growing, compact, and freely branching. Flowering is early, year-round, and exceptionally abundant. A mature plant is an 8-inch diameter pot often has 6–10 open flowers. Very dark leaves and numerous dark red flowers held above the foliage make it an attractive flowering pot plant.

Comparison with known cultivars:

*Note.*—These comparisons were made from plants grown under the same conditions in Altha, Fla.

*Anthurium 'Lady Jane' (unpatented).*—'Ruth Morat' has darker-colored, larger flowers, more consistently held above the foliage.

*Anthurium 'Rosa' (unpatented).*—'Ruth Morat' is more compact, has darker green leaves, and smaller flowers. Flower color is distinctly more red than 'Rosa'.

*Anthurium 'Southern Blush' a plant of the University of Florida (unpatented).*—'Ruth Morat' has darker, thicker leaves, and larger, darker flowers, better preserving their color with aging.

I claim:

1. A new and distinct hybrid Anthurium plant substantially as herein shown and described, characterized particularly as to novelty by its fast growing, compact and freely branching form, early and year-round abundant flowering, a mature plant frequently having six to ten open dark red flowers, the leaves being very dark, and the flowers held above the foliage to provide an attractive pot plant.

* * * * *